(12) United States Patent
Schneider et al.

(10) Patent No.: US 10,031,141 B2
(45) Date of Patent: Jul. 24, 2018

(54) VEGF POLYMORPHISMS AND ANTI-ANGIOGENESIS THERAPY

(75) Inventors: Bryan P. Schneider, Avon, IN (US);
Milan Radovich, Indianapolis, IN (US);
George W. Sledge, Indianapolis, IN (US)

(73) Assignee: Genentech, Inc., South San Francisco, CA (US)

( * ) Notice: Subject to any disclaimer, the term of this patent is extended or adjusted under 35 U.S.C. 154(b) by 830 days.

(21) Appl. No.: 12/745,291

(22) PCT Filed: Nov. 26, 2008

(86) PCT No.: PCT/US2008/084933
§ 371 (c)(1),
(2), (4) Date: Mar. 24, 2011

(87) PCT Pub. No.: WO2009/073540
PCT Pub. Date: Jun. 11, 2009

(65) Prior Publication Data
US 2011/0176993 A1 Jul. 21, 2011

Related U.S. Application Data

(60) Provisional application No. 61/038,699, filed on Mar. 21, 2008, provisional application No. 60/991,616, filed on Nov. 30, 2007.

(51) Int. Cl.
| | | |
|---|---|---|
| *C12Q 1/68* | (2018.01) |
| *G01N 33/574* | (2006.01) |
| *C12Q 1/6883* | (2018.01) |
| *G01N 33/68* | (2006.01) |

(52) U.S. Cl.
CPC ......... *G01N 33/574* (2013.01); *C12Q 1/6883* (2013.01); *G01N 33/6893* (2013.01); *C12Q 2600/106* (2013.01); *C12Q 2600/118* (2013.01); *C12Q 2600/142* (2013.01); *C12Q 2600/156* (2013.01); *G01N 2800/321* (2013.01); *G01N 2800/50* (2013.01); *G01N 2800/52* (2013.01)

(58) Field of Classification Search
None
See application file for complete search history.

(56) References Cited

U.S. PATENT DOCUMENTS

2007/0207486 A1  9/2007  Lenz

FOREIGN PATENT DOCUMENTS

| JP | 2007-20563 | 2/2007 |
| WO | WO 2006/086544 | 8/2006 |
| WO | WO-2006/086544 A2 | 8/2006 |
| WO | WO 2007/022101 | 2/2007 |
| WO | WO-2007/022101 A2 | 2/2007 |

OTHER PUBLICATIONS

Pasqualetti et al; Pharmacogenomics; Jan. 2007, vol. 8, pp. 49-66.*
Koukourakis et al; Lung Cancer, vol. 46, pp. 293-298; 2004.*
Loomis et al; Annals of Oncology, vol. 21, pp. vi26; 2010.*
Hegele (Arterioscler. Thromb. Vasc. Biol.; 2002, vol. 22, pp. 1058-1061).*
Lucentini (The Scientist; 2004, vol. 24, p. 20).*
Juppner; Bone, vol. 17; 1995, pp. 39S-40S.*
Awata et al., "A common polymorphism in the 5'-untranslated region of the VEGF gene is associated with diabetic retinopathy in type 2 diabetes," Diabetes. 51(5):1635-1639 (2002).
Koukourakis et al., "VEGF gene sequence variation defines VEGF gene expression status and angiogenic activity in non-small cell lung cancer," Lung Cancer. 46(3):293-298 (2004).
Mateo et al., "Case-control study of vascular endothelial growth factor (VEGF) genetic variability in Alzheimer's disease," Neurosci Lett. 401:171-173 (2006).
Pande et al., "Hypertension secondary to anti-angiogenic therapy: experience with bevacizumab," Anticancer Res. 27(5B):3465-3470 (2007).
Pasqualetti et al., "Vascular endothelial growth factor pharmacogenetics: a new perspective for anti-angiogenic therapy," Pharmacogenomics. 8(1):49-66 (2007).
Office Action for Japanese Patent Application No. 2010-536182, dated Jul. 29, 2013 (10 pages).
Doi et al., "Non-association of VEGF genetic polymorphisms in promoter—5' UTR with end-stage renal disease," Nephrol Dial Transplant. 21:1124-1125 (2006).
Errera et al., "Functional vascular endothelial growth factor -634G>C SNP is associated with proliferative diabetic retinopathy: A case-control study in a Brazilian population of European ancestry," Diabetes Care. 30(2):275-279 (2007).
Summers et al., "VEGF -460 genotype plays an important role in progression to chronic kidney disease stage 5," Nephrol Dial Transplant. 20:2427-2432 (2005).
Examination Report for Australian Patent Application No. 2008334070, dated Jun. 22, 2013 (5 pages).
Kim et al., "Genetic polymorphism of vascular endothelial growth factor (VEGF C936T) in the Korean population," Korean Journal of Biological Sciences 7:261-264, 2003.
Schneider et al., "Association of vascular endothelial growth factor and vascular endothelial growth factor receptor-2 genetic polymorphisms with outcome in a trial of paclitaxel compared with paclitaxel plus bevacizumab in advanced breast cancer: ECOG 2100," Journal of Clinical Oncology 26:4672-4678, 2008.
Zhu et al., "Anti-vascular endothelial growth factor (VEGF) therapy: A new cause of hypertension," Current Hypertension Reviews 3:149-155, 2007.
International Search Report and Written Opinion completed Feb. 23, 2009, dated Jun. 17, 2009, in corresponding PCT Application No. PCT/US2008/084933.
Examination report for New Zealand Patent Application No. 585432 dated Feb. 8, 2011.
Translation of the Office Action from Israeli Patent Application No. 205748 dated Feb. 13, 2012.
Opposition to European Patent Application No. 08857392.8, submitted May 30, 2011 (19 pages).

(Continued)

*Primary Examiner* — Jehanne S Sitton
(74) *Attorney, Agent, or Firm* — Clark and Elbing LLP.; Karen L. Elbing

(57) ABSTRACT

Methods for determining whether a patient in at particular risk of hypertension associated with anti-VEGF treatment or has a greater likelihood of benefiting from anti-VEGF therapy by screening a sample isolated from the patient for specific genomic polymorphisms.

3 Claims, No Drawings

(56) References Cited

OTHER PUBLICATIONS

Schneider et al., "Association of polymorphisms of angiogenesis genes with breast cancer," Breast Cancer Res Treat. 111(1):157-63 (2008).
Stevens et al., "Haplotype analysis of the polymorphic human vascular endothelial growth factor gene promoter," Cancer Res. 63:812-6 (2003).
Gray et al., "Independent review of E2100: a phase III tril of bevacizumab plus paclitaxel versus paclitaxel in women with metastatic breast cancer," J Clin Oncol. 29(30):4966-72 (2009).
O'Rourke, "Finding an avastin biomarker: an elusive target for a decade, investigators hvae searched in vain for a predictive bevacizumab marker," Clin Oncol News, Solid Tumor. 7(2), (32 pages) (2012).
Kim et al., "Promoter polymorphisms of the vascular endothelial growth factor gene is associated with an osteonecrosis of the femoral head in the Korean population," Osteoarthritis and Cartilage. 16(3):287-91 (2008). Abstract Only.
Rueda et al., "A functional variant of vascular endothelial growth factor is associated with severe ischemic complications in giant cell arteritis." J Rheum. 32(9):1737-41 (2005). Abstract Only.
Jin et al., "Vascular endothelial growth factor polymorphisms in relation to breast cancer development and prognosis," Clin Cancer Res. 11(10):3647-3653 (2005).
Kariyazono et al., "Association of vascular endothelial growth facor (VEGF) and VEGF receptor gene polymorphisms with coronary artery lesions of kawasaki disease," Ped Res. 56(6):953-9 (2004).
Salvarani et al., "Vascular endothelial growth factor gene polymorphisms in Behçet's disease," J Rheumatol 31(9):1785-9 (2004). abstract only.
Suganthalakshmi et al., "Association of VEGF and eNOS gene polymorphisms in type 2 diabetic retinopathy," Mol Vis 12:336-41 (2006).
Decision High Court No. 11 C00127, *Bayer and Regeneron v. Genentech*, dated Mar. 22, 2012 (56 pages).
"Paclitaxel with or without bevacizumab in treating patients with locally recurrent or metastatic breast cancer," Study 2100 ecog, Identifier NCT00028990. ClinicalTrials.gov, accessed May 25, 2012 (7 pages).
Han et al., "VEGF gene polymorphisms and susceptibility to rheumatoid arthritis," Rheumatology. 43(9):1173-7 (2004).
Search Report and Written Opinion for European Patent Application No. 11179025.9, dated Dec. 3, 2012 (11 pages).
Thickett et al., "Vascular endothelial growth factor may contribute to increased vascular permeability in acute respiratory distress syndrome," Am J Respir Crit Care Med. 164(9):1601-5 (2001).
Zhai et al., "Genotypes and haplotypes of the VEGF gene are associated with higher mortality and lower VEGF plasma levels in patients with ARDS," Thorax. 62(8):718-22 (2007).
Notice of Reasons for Rejection for Japanese Patent Application No. 2014-014126, dated Apr. 6, 2015 (10 pages).
Notice of Preliminary Rejection for Korean Application No. 10-2010-7011781, dated Apr. 27, 2015 (19 pages).
First Examination Report for New Zealand Patent Application No. 722920, dated Sep. 1, 2016 (3 pages).
Hefler et al., "Vascular endothelial growth factor gene polymorphisms are associated with prognosis in ovarian cancer," Clin Cancer Res. 13(3):898-901 (2007).
Jacobs et al., "Polymorphisms in the vascular endothelial growth factor gene and breast cancer in the Cancer Prevention Study II cohort," Breast Cancer Res. 8(2):R22 (2006) (6 pages).
Szeto et al., "Genetic polymorphism of VEGF: Impact on longitudinal change of peritoneal transport and survival of peritoneal dialysis patients," Kidney Int. 65(5):1947-55 (2004).
Office Action for Russian Patent Application No. 2013107095, dated Apr. 7, 2017 (9 pages).

* cited by examiner

VEGF POLYMORPHISMS AND ANTI-ANGIOGENESIS THERAPY

CROSS REFERENCE TO RELATED APPLICATION

This application is a 371 of International Application No. PCT/US2008/084933, filed 26 Nov. 2008, and claims the benefit of U.S. Provisional Application No. 60/991,616, filed 30 Nov. 2007, and U.S. Provisional Application No. 61/038,699, filed 21 Mar. 2008, the disclosures of which are incorporated herein by reference in their entirety.

FIELD OF THE INVENTION

This invention relates in general to treatment of human diseases and disorders associated with anti-angiogenesis therapy. More specifically, the invention relates to anti-angiogenesis therapy of cancer, either alone or in combination with other anti-cancer therapies.

BACKGROUND OF THE INVENTION

Cancer remains one of the most deadly threats to human health, affecting over 1 million new patients each year in the United States. Solid tumors are responsible for most of those deaths. Although there have been significant advances in the medical treatment of certain cancers, current methods of treatment are relatively non-selective: surgery removes the diseased tissue; radiotherapy shrinks solid tumors; and chemotherapy kills rapidly dividing cells. These treatments may result in numerous side effects, in some cases so severe as to limit the dosage that can be given and thus preclude the use of potentially effective drugs.

Angiogenesis is an important cellular event in which vascular endothelial cells proliferate, prune and reorganize to form new vessels from preexisting vascular networks. Angiogenesis is essential for the growth of most primary tumors and their subsequent metastasis. Vascular endothelial cell growth factor (VEGF), which is also termed VEGF-A or vascular permeability factor (VPF), has been reported as a pivotal regulator of both normal and abnormal angiogenesis. Ferrara and Davis-Smyth (1997) *Endocrine Rev.* 18:4-25; Ferrara (1999) *J. Mol. Med.* 77:527-543.

The anti-VEGF antibody "Bevacizumab", also known as "BV", "rhuMAb VEGF", or "Avastin®", is a recombinant humanized anti-VEGF monoclonal antibody generated according to Presta et al. (1997) *Cancer Res.* 57:4593-4599, which is currently approved in the U.S. for the treatment of metastatic colorectal cancer, non-small cell lung cancer, and metastatic breast cancer. Like other cancer treatments, Avastin® therapy is associated with certain side-effects, including an increased risk of hypertension.

Genetic polymorphisms occur in a population when different alleles in particular genes result in different phenotypes. Such polymorphisms may play a role in determining the efficacy and safety of therapeutic drugs. For example, specific polymorphisms in VEGF have been shown to be associated with the incidence of breast cancer. Schneider et al. (2008) *Breast Cancer Research and Treatment* 111:157-63.

Identification of additional polymorphisms predictive of the efficacy or safety of particular therapies may be used to better tailor therapies to those patients who would best benefit from them.

SUMMARY OF THE INVENTION

The present invention is based in part on the identification of polymorphisms in VEGF that are predictive of an increased likelihood of benefiting from treatment with a VEGF antagonist and/or an increased risk of hypertension in patients undergoing anti-VEGF therapy, including with Avastin®.

In one aspect, the invention provides a method of predicting whether a patient is at increased risk of hypertension associated with treatment with a VEGF antagonist, comprising screening a sample isolated from the patient for a genomic polymorphism selected from VEGF (−1498C/T) and VEGF (−634G/C), wherein the patient is at increased risk of hypertension associated with treatment with a VEGF antagonist if the corresponding genotype comprises VEGF (−1498C) or VEGF (−634G). In some embodiments, the VEGF antagonist is an anti-VEGF antibody, e.g. bevacizumab. In some embodiments, the treatment further comprises administering an anti-neoplastic composition. In some embodiments, the patient is being treated for cancer, e.g. breast cancer.

In another aspect, the invention provides a kit for predicting whether a patient is at increased risk of hypertension associated with treatment with a VEGF antagonist comprising a first oligonucleotide and a second oligonucleotides specific for a polymorphism in VEGF selected from the group consisting of: VEGF (−1498C/T) and VEGF (−634G/C). In some embodiments the oligonucleotides in the kit are useful for amplification of the region of VEGF comprising one of these polymorphisms.

In another aspect, the invention provides a method of predicting whether a patient has an increased likelihood of benefiting from treatment with a VEGF antagonist, comprising screening a sample isolated from the patient for a genomic polymorphism at VEGF (−2578C/A) or VEGF (−1154G/A), wherein the patient has an increased likelihood of benefiting from treatment with a VEGF antagonist if the corresponding genotype comprises VEGF (−2578AA) or VEGF (1154AA). In some embodiments, the VEGF antagonist is an anti-VEGF antibody, e.g. bevacizumab. In some embodiments, the treatment further comprises administering an anti-neoplastic composition. In some embodiments, the patient is being treated for cancer, e.g. breast cancer.

In another aspect, the invention provides a kit for predicting whether a patient has an increased likelihood of benefiting from treatment with a VEGF antagonist comprising a first oligonucleotide and a second oligonucleotides specific for a polymorphism in VEGF selected from the group consisting of: VEGF (−2578C/A) and VEGF (−1154G/A). In some embodiments the oligonucleotides in the kit are useful for amplification of the region of VEGF comprising one of these polymorphisms.

DETAILED DESCRIPTION OF THE PREFERRED EMBODIMENTS

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), and March, *Advanced Organic Chemistry Reactions, Mechanisms and Structure* 4th ed., John Wiley & Sons (New York, N.Y. 1992), provide one skilled in the art with a general guide to many of the terms used in the present application.

All references cited herein, including patent applications and publications, are incorporated by reference in their entirety.

Definitions

As used herein, the singular forms "a", "an" and "the" include the plural unless the context clearly dictates otherwise. For example, "a" cell will also include "cells".

The term "comprising" is intended to mean that the compositions and methods include the recited elements, but do not exclude others.

The terms "VEGF" and "VEGF-A" are used interchangeably to refer to the 165-amino acid vascular endothelial cell growth factor and related 121-, 189-, and 206-amino acid vascular endothelial cell growth factors, as described by Leung et al. *Science*, 246:1306 (1989), and Houck et al. *Mol. Endocrin.*, 5:1806 (1991), together with the naturally occurring allelic and processed forms thereof. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)" or "VEGF$_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

An "anti-VEGF antibody" is an antibody that binds to VEGF with sufficient affinity and specificity. Preferably, the anti-VEGF antibody of the invention can be used as a therapeutic agent in targeting and interfering with diseases or conditions wherein the VEGF activity is involved. An anti-VEGF antibody will usually not bind to other VEGF homologues such as VEGF-B or VEGF-C, or other growth factors such as PlGF, PDGF or bFGF. A preferred anti-VEGF antibody is a monoclonal antibody that binds to the same epitope as the monoclonal anti-VEGF antibody A4.6.1 produced by hybridoma ATCC HB 10709. More preferably the anti-VEGF antibody is a recombinant humanized anti-VEGF monoclonal antibody generated according to Presta et al. (1997) *Cancer Res.* 57:4593-4599, including but not limited to the antibody known as bevacizumab (BV; Avastin®).

A "VEGF antagonist" refers to a molecule capable of neutralizing, blocking, inhibiting, abrogating, reducing or interfering with VEGF activities including its binding to one or more VEGF receptors. VEGF antagonists include anti-VEGF antibodies and antigen-binding fragments thereof, receptor molecules and derivatives which bind specifically to VEGF thereby sequestering its binding to one or more receptors, anti-VEGF receptor antibodies and VEGF receptor antagonists such as small molecule inhibitors of the VEGFR tyrosine kinases.

The term "antibody" is used in the broadest sense and includes monoclonal antibodies (including full length or intact monoclonal antibodies), polyclonal antibodies, multivalent antibodies, multispecific antibodies (e.g., bispecific antibodies), and antibody fragments so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) or Marks et al., *J. Mol. Biol.* 222:581-597 (1991), for example.

A "disorder" is any condition that would benefit from treatment with the antibody. This includes chronic and acute disorders or diseases including those pathological conditions which predispose the mammal to the disorder in question. Non-limiting examples of disorders to be treated herein include benign and malignant tumors; leukemias and lymphoid malignancies; neuronal, glial, astrocytal, hypothalamic and other glandular, macrophagal, epithelial, stromal and blastocoelic disorders; and inflammatory, angiogenic and immunologic disorders.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the overall survival (OS), progression free survival (PFS), time to disease progression (TTP), the response rates (RR), duration of response, and/or quality of life.

"Treatment" refers to both therapeutic treatment and prophylactic or preventative measures. Those in need of treatment include those already with the disorder as well as those in which the disorder is to be prevented.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

The term "anti-neoplastic composition" refers to a composition useful in treating cancer comprising at least one active therapeutic agent capable of inhibiting or preventing tumor growth or function, and/or causing destruction of tumor cells. Therapeutic agents suitable in an anti-neoplastic composition for treating cancer include, but not limited to, chemotherapeutic agents, radioactive isotopes, toxins, cytokines such as interferons, and antagonistic agents targeting cytokines, cytokine receptors or antigens associated with tumor cells. Preferably the therapeutic agent is a chemotherapeutic agent.

A "chemotherapeutic agent" is a chemical compound useful in the treatment of cancer.

An "isolated" nucleic acid molecule is a nucleic acid molecule that is identified and separated from at least one contaminant nucleic acid molecule with which it is ordinarily associated in the natural source of the polypeptide nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the polypeptide where, for example, the nucleic acid molecule is in a chromosomal location different from that of natural cells.

The term "polymorphism" refers to a location in the sequence of a gene which varies within a population. A polymorphism is comprised of different "alleles". The location of such a polymorphism is identified by its position in the gene and the different bases that are found there. For example, VEGF −1498C/T indicates that there is variation between C and T at position −1498 in the VEGF gene. The two possible variants, C and T, are two different alleles. Because the genotype is comprised of two separate alleles, any of several possible variants may be observed in any one individual (e.g. for this example, CC, CT, or TT).

The term "genotype" refers to the specific alleles of a certain gene in a cell or tissue sample. In the example above, CC, CT, or TT are possible genotypes at the VEGF −1498C/T polymorphism.

The term "sample" includes a cell or tissue sample taken from a patient. For example, a sample may include a tumor sample, a sample of normal tissue corresponding to the tumor type, a sample of tissue taken from the area surrounding the tumor, or blood cells.

Identification of the particular genotype in a sample may be performed by any of a number of methods well known to one of skill in the art. For example, identification of the polymorphism can be accomplished by cloning of the allele and sequencing it using techniques well known in the art. Alternatively, the gene sequences can be amplified from genomic DNA, e.g. using PCR, and the product sequenced. Several non-limiting methods for analyzing a patient's DNA for mutations at a given genetic locus are described below.

DNA microarray technology, e.g., DNA chip devices and high-density microarrays for high-throughput screening applications and lower-density microarrays, may be used. Methods for microarray fabrication are known in the art and include various inkjet and microjet deposition or spotting technologies and processes, in situ or on-chip photolithographic oligonucleotide synthesis processes, and electronic DNA probe addressing processes. The DNA microarray hybridization applications has been successfully applied in the areas of gene expression analysis and genotyping for point mutations, single nucleotide polymorphisms (SNPs), and short tandem repeats (STRs). Additional methods include interference RNA microarrays and combinations of microarrays and other methods such as laser capture microdisection (LCM), comparative genomic hybridization (CGH) and chromatin immunoprecipitation (ChIP). See, e.g., He et al. (2007) *Adv. Exp. Med. Biol.* 593:117-133 and Heller (2002) *Annu. Rev. Biomed. Eng.* 4:129-153. Other methods include PCR, xMAP, invader assay, mass spectrometry, and pyrosequencing (Wang et al. (2007) 593:105-106).

Another detection method is allele specific hybridization using probes overlapping the polymorphic site and having about 5, or alternatively 10, or alternatively 20, or alternatively 25, or alternatively 30 nucleotides around the polymorphic region. For example, several probes capable of hybridizing specifically to the allelic variant are attached to a solid phase support, e.g., a "chip". Oligonucleotides can be bound to a solid support by a variety of processes, including lithography. Mutation detection analysis using these chips comprising oligonucleotides, also termed "DNA probe arrays" is described e.g., in Cronin et al. (1996) *Human Mutation* 7:244.

In other detection methods, it is necessary to first amplify at least a portion of the gene prior to identifying the allelic variant. Amplification can be performed, e.g., by PCR and/or LCR or other methods well known in the art.

In some cases, the presence of the specific allele in DNA from a subject can be shown by restriction enzyme analysis. For example, the specific nucleotide polymorphism can result in a nucleotide sequence comprising a restriction site which is absent from the nucleotide sequence of another allelic variant.

In a further embodiment, protection from cleavage agents (such as a nuclease, hydroxylamine or osmium tetroxide and with piperidine) can be used to detect mismatched bases in RNA/RNA DNA/DNA, or RNA/DNA heteroduplexes (see, e.g., Myers et al. (1985) *Science* 230:1242). In general, the technique of "mismatch cleavage" starts by providing heteroduplexes formed by hybridizing a control nucleic acid, which is optionally labeled, e.g., RNA or DNA, comprising a nucleotide sequence of the allelic variant of the gene with a sample nucleic acid, e.g., RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with S1 nuclease to enzymatically digest the mismatched regions. Alternatively, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, U.S. Pat. No. 6,455,249, Cotton et al. (1988) *Proc. Natl. Acad. Sci. USA* 85:4397; Saleeba et al. (1992) *Meth. Enzymol.* 217:286-295.

Alterations in electrophoretic mobility may also be used to identify the particular allelic variant. For example, single strand conformation polymorphism (SSCP) may be used to detect differences in electrophoretic mobility between mutant and wild type nucleic acids (Orita et al. (1989) *Proc Natl. Acad. Sci USA* 86:2766; Cotton (1993) *Mutat. Res.* 285:125-144 and Hayashi (1992) *Genet. Anal. Tech. Appl.* 9:73-79). Single-stranded DNA fragments of sample and control nucleic acids are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) *Trends Genet.* 7:5).

The identity of the allelic variant may also be obtained by analyzing the movement of a nucleic acid comprising the polymorphic region in polyacrylamide gels containing a gradient of denaturant, which is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) *Biophys. Chem.* 265:1275).

Examples of techniques for detecting differences of at least one nucleotide between 2 nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotide hybridization techniques may be used for the detection of the nucleotide changes in the polymorphic region of the gene. For example, oligonucleotides having the nucleotide sequence of the specific allelic variant are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant invention. Oligonucleotides used as primers for specific amplification may carry the allelic variant of interest in the center of the molecule (so that amplification depends on differential hybridization) (Gibbs et al. (1989) *Nucl. Acids Res.* 17:2437-2448) or at the extreme 3' end of one primer where, under appropriate conditions, mismatch can prevent, or reduce polymerase extension (Prossner (1993) Tibtech 11:238 and Newton et al. (1989) *Nucl. Acids Res.* 17:2503). This technique is also termed "PROBE" for Probe Oligo Base. Extension. In addition it may be desirable to introduce a novel restriction site in the region of the mutation to create cleavage-based detection (Gasparini et al. (1992) *Mol. Cell. Probes* 6:1).

In another embodiment, identification of the allelic variant is carried out using an oligonucleotide ligation assay (OLA), as described, e.g., in U.S. Pat. No. 4,998,617 and in Laridegren, U. et al. *Science* 241:1077-1080 (1988). The OLA protocol uses two oligonucleotides which are designed to be capable of hybridizing to abutting sequences of a single strand of a target. One of the oligonucleotides is linked to a separation marker, e.g., biotinylated, and the other is detectably labeled, If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al. (1990) *Proc. Natl. Acad. Sci. USA* 87:8923-8927). In this method, PCR is used to achieve the exponential amplification of target DNA, which is then detected using OLA.

The invention provides methods for detecting a single nucleotide polymorphism (SNP) in VEGF. Because single nucleotide polymorphisms are flanked by regions of invariant sequence, their analysis requires no more than the determination of the identity of the single variant nucleotide and it is unnecessary to determine a complete gene sequence for each patient. Several methods have been developed to facilitate the analysis of SNPs.

The single base polymorphism can be detected by using a specialized exonuclease-resistant nucleotide, as disclosed, e.g., in U.S. Pat. No. 4,656,127. According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

A solution-based method may also be used for determining the identity of the nucleotide of the polymorphic site (WO 91/02087). As above, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method is described in WO 92/15712. This method uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. The method is usually a heterogeneous phase assay, in which the primer or the target molecule is immobilized to a solid phase.

Many other primer-guided nucleotide incorporation procedures for assaying polymorphic sites in DNA have been described (Komher, J. S. et al. (1989) *Nucl. Acids. Res.* 17:7779-7784; Sokolov, B. P. (1990) *Nucl. Acids Res.* 18:3671; Syvanen, A. -C., et al. (1990) Genomics 8:684-692; Kuppuswamy, M. N. et al. (1991) *Proc. Natl. Acad. Sci. USA* 88:1143-1147; Prezant, T. R. et al. (1992) *Hum. Mutat.* 1: 159-164; Ugozzoli, L. et al. (1992) *GATA* 9:107-112; Nyren, P. et al. (1993) *Anal. Biochem.* 208:171-175). These methods all rely on the incorporation of labeled deoxynucleotides to discriminate between bases at a polymorphic site.

Moreover, it will be understood that any of the above methods for detecting alterations in a gene or gene product or polymorphic variants can be used to monitor the course of treatment or therapy.

The methods described herein may be performed, for example, by utilizing pre-packaged diagnostic kits, such as those described below, comprising at least one probe or primer nucleic acid, which may be conveniently used, e.g., to determine whether a subject is at risk of developing hypertension associated with treatment with a VEGF-antagonist.

Sample nucleic acid for use in the above-described diagnostic and prognostic methods can be obtained from any cell type or tissue of a subject. For example, a subject's bodily fluid (e.g. blood) can be obtained by known techniques. Alternatively, nucleic acid tests can be performed on dry samples (e.g., hair or skin).

The invention described herein relates to methods and compositions for determining and identifying the allele present at the VEGF locus. This information is useful to predict the level of risk of developing hypertension associated with treatment with a VEGF-antagonist. Probes can be used to directly determine the genotype of the sample or can be used simultaneously with or subsequent to amplification. The term "probes" includes naturally occurring or recombinant single- or double-stranded nucleic acids or chemically synthesized nucleic acids. They may be labeled by nick translation, Klenow fill-in reaction, PCR or other methods known in the art. Probes of the present invention, their preparation and/or labeling are described in Sambrook et al. (1989) supra. A probe can be a polynucleotide of any length suitable for selective hybridization to a nucleic acid containing a polymorphic region of the invention. Length of the probe used will depend, in part, on the nature of the assay used and the hybridization conditions employed.

Labeled probes also can be used in conjunction with amplification of a polymorphism. (Holland et al. (1991) *Proc. Natl. Acad. Sci. USA* 88:7276-7280). U.S. Pat. No. 5,210,015 describes fluorescence-based approaches to provide real time measurements of amplification products during PCR. Such approaches have either employed intercalating dyes (such as ethidium bromide) to indicate the amount of double-stranded DNA present, or they have employed probes containing fluorescence-quencher pairs (also referred to as the "Taq-Man" approach) where the probe is cleaved during amplification to release a fluorescent molecule whose concentration is proportional to the amount of double-stranded DNA present. During amplification, the probe is digested by the nuclease activity of a polymerase when hybridized to the target sequence to cause the fluorescent molecule to be separated from the quencher molecule, thereby causing fluorescence from the reporter molecule to appear. The Taq-Man approach uses a probe containing a reporter molecule-quencher molecule pair that specifically anneals to a region of a target polynucleotide containing the polymorphism.

Probes can be affixed to surfaces for use as "gene chips." Such gene chips can be used to detect genetic variations by a number of techniques known to one of skill in the art. In one technique, oligonucleotides are arrayed on a gene chip for determining the DNA sequence of a by the sequencing by hybridization approach, such as that outlined in U.S. Pat. Nos. 6,025,136 and 6,018,041. The probes of the invention also can be used for fluorescent detection of a genetic sequence. Such techniques have been described, for example, in U.S. Pat. Nos. 5,968,740 and 5,858,659. A probe also can be affixed to an electrode surface for the electrochemical detection of nucleic acid sequences such as described in U.S. Pat. No. 5,952,172 and by Kelley, S. O. et al. (1999) *Nucl. Acids Res.* 27:4830-4837.

Additionally, the isolated nucleic acids used as probes or primers may be modified to become more stable. Exemplary nucleic acid molecules which are modified include phosphoramidate, phosphothioate and methylphosphonate analogs of DNA (see also U.S. Pat. Nos. 5,176,996; 5,264,564 and 5,256,775).

As set forth herein, the invention also provides diagnostic methods for determining the type of allelic variant of a polymorphic region present in VEGF. In some embodiments, the methods use probes or primers comprising nucleotide sequences which are complementary to the polymorphic region of VEGF. Accordingly, the invention provides kits for performing these methods.

In some embodiments, the invention provides a kit for determining whether a subject is at risk of developing hypertension associated with treatment with a VEGF-antagonist. In some embodiments, the invention provides a kit for determining whether a subject has a greater likelihood of benefiting from anti-VEGF therapy. Such kits contain one of more of the compositions described above and instructions for use. As an example only, the invention also provides kits for determining whether a patient is at risk of developing hypertension associated with treatment with a VEGF-antagonist containing a first and second oligonucleotide specific for a polymorphic region of VEGF, e.g., VEGF (−2578 C/A), VEGF (−1498C/T), VEGF (−1154G/A) or VEGF (−634G/C). As another example, the invention also provides kits for determining whether a subject has a greater likelihood of benefiting from anti-VEGF therapy containing a first and second oligonucleotide specific for a polymorphic region of VEGF, e.g., VEGF (−2578C/A) or VEGF (−1154G/A). Oligonucleotides "specific for" a genetic locus bind either to the polymorphic region of the locus or bind adjacent to the polymorphic region of the locus. For oligonucleotides that are to be used as primers for amplification, primers are adjacent if they are sufficiently close to be used to produce a polynucleotide comprising the polymorphic region. In one embodiment, oligonucleotides are adjacent if they bind within about 1-2 kb, e.g. less than 1 kb from the polymorphism. Specific oligonucleotides are capable of hybridizing to a sequence, and under suitable conditions will not bind to a sequence differing by a single nucleotide.

The kit can comprise at least one probe or primer which is capable of specifically hybridizing to the polymorphic region of the VEGF and instructions for use. The kits usually comprise at least one of the above described nucleic acids. Kits for amplifying at least a portion of VEGF generally comprise two primers, at least one of which is capable of hybridizing to the allelic variant sequence. Such kits are suitable for detection of genotype by, for example, fluorescence detection, by electrochemical detection, or by other detection.

Oligonucleotides, whether used as probes or primers, contained in a kit can be detectably labeled. Labels can be detected either directly, for example for fluorescent labels, or indirectly. Indirect detection can include any detection method known to one of skill in the art, including biotin-avidin interactions, antibody binding and the like. Fluorescently labeled oligonucleotides also can contain a quenching molecule. Oligonucleotides can be bound to a surface. In some embodiments, the surface is silica or glass. In some embodiments, the surface is a metal electrode.

Yet other kits of the invention comprise at least one reagent necessary to perform the assay. For example, the kit can comprise an enzyme. Alternatively the kit can comprise a buffer or any other necessary reagent.

The kits can include all or some of the positive controls, negative controls, reagents, primers, sequencing markers, probes and antibodies described herein for determining the subject's genotype in the polymorphic region of the VEGF.

The following example is intended merely to illustrate the practice of the present invention and is not provided by way of limitation. The disclosures of all patent and scientific literatures cited herein are expressly incorporated in their entirety by reference.

EXAMPLE

Example 1. Genetic Polymorphisms in VEGF and their Association with Outcome

E2100 was a Phase III, Intergroup trial that demonstrated an improvement in progression free survival (PFS) and response rate (RR) when adding bevacizumab to paclitaxel for women with previously untreated metastatic breast cancer. There was significantly more hypertension and proteinuria seen in women who received bevacizumab.

Samples

We performed a retrospective trial of data from the E2100 trial of Avastin for breast cancer. The data set included 673 eligible patients with 623 disease progression events and 483 deaths. Of these, we genotyped paraffin-embedded tumor blocks from 363 eligible cases (median follow-up of 43 months). In addition, 377 eligible cases were available for VEGF IHC and 341 were available for VEGFR-2 IHC. All specimens were analyzed "blind" without patient identifiers or clinical outcome information.

Polymorphisms

The polymorphisms we tested are shown in Table 1.

TABLE 1

Single Nucleotide Polymorphisms (SNPs) Tested

| Gene | Single Nucleotide Polymorphism (SNP) | Location | Caucasian: Frequency of rare allele[1] | African American: Frequency of rare allele[1] |
|---|---|---|---|---|
| VEGF | −2578 C/A | Promoter | A = 49% | A = 24% |
| | −1498 C/T | Promoter | C = 49% | C = 33% |

TABLE 1-continued

Single Nucleotide Polymorphisms (SNPs) Tested

| Gene | Single Nucleotide Polymorphism (SNP) | Location | Caucasian: Frequency of rare allele[1] | African American: Frequency of rare allele[1] |
|---|---|---|---|---|
| | −1154 G/A | Promoter | A = 33% | A = 10% |
| | −634 G/C | 5' UTR | C = 32% | C = 35% |
| | 936 C/T | 3' UTR | T = 15% | T = 13% |
| VEGFR-2 | 889 G/A (V297I) | Exon 7 | A = 9% | A = 20% |
| | 1416 A/T (Q472H) | Exon 11 | T = 25% | T = 10% |

These polymorphisms were chosen because these genes are known to modulate angiogenesis: 1) they are involved in the angiogenesis pathway; 2) they had an established genetic polymorphism; 3) the frequency of the polymorphism was high enough that its impact on drug response at a population level would be meaningful; and/or 4) the polymorphism could alter the function of the gene in a biologically relevant manner.

Genotyping of SNPs

DNA was extracted from 20 micro-meter paraffin embedded tissue sections using the DNeasy® Tissue kit (Qiagen, Valencia, Calif.). SNPs were genotyped with Taqman®-based Real Time-PCR. Details for each SNP have been previously described in Schneider, et al. (2007) "Association of polymorphisms of angiogenesis genes with breast cancer." *Breast Cancer Res. Treat.* Overall, genotype was successfully determined in 88.2% of cases. This varied based on SNP analyzed and ranged from 82% to 92% success rate. For all SNPs combined, 50% were accurately assessed from the control arm and 50% from the combination arm.

Assessment of Protein Expression

Protein expression for both VEGF and VEGFR-2 were assessed by IHC from the submitted tumor block. For VEGF assessment, slides were deparaffinized, rehydrated and placed in a vegetable steamer with citrate buffer at pH of 6.0 for 30 minutes. After slides cooled to room temperature they were washed in two changes distilled water followed by two changes of phosphate buffered saline (PBST) with 0.05% Tween™ 20 (Fisher Scientific, Pittsburgh Pa.). Slides were then placed on a Dako Autostainer (Dako Cytomation, Carpinteria Calif.). Slides were incubated with peroxidase blocking solution (Dako, S2001) for 10 minutes followed by three changes of PBST for a minimum of 10 minutes total. Slides were then sequentially incubated with anti-VEGF antibody (VG1, Lab Vision, Fremont Calif.) diluted 1:100 for 60 minutes, Dako Envision+(Dako, K4001) for 60 minutes and DAB Substrate-Chromogen System (Dako, K3466), with three changes of PBST between each step. Slides were counterstained with Harris hematoxylin (Fisher) dehydrated, cleared and had a cover-slip placed. A VEGF-inv score was calculated by estimating the percentage of invasive tumor cells with cytoplasmic VEGF staining from the entire slide.

For VEGFR-2 IHC, formalin-fixed paraffin-embedded breast tumor sections were first deparaffinized and rehydrated. Next, antigen retrieval was executed at 98° C. for 20 minutes in Target Retrieval Solution pH of 9.0 (S2367, Dako, Carpenteria, Calif.). Dual Endogenous Enzyme Block (K4065, EnVision™+Dual Link System-HRP, Dako) was then applied for 5 minutes at room temperature. Anti-VEGFR-2 clone 55B11 rabbit monoclonal antibody (#2479, Cell Signaling Tech., Danvers, Mass.) was administered at 1:20 for 2 hours at room temperature. Signal development with DAB was conducted by the protocol for the EnVision+ kit with minor modifications. Counterstaining was completed with Hematoxylin QS (H-3404, Vector, Burlingame, Calif.) followed by dehydration and cover-slipping. Human placenta or liver sections were used as positive controls. Omission of the primary antibody and substitution with rabbit IgG (X0936, Dako) served as negative controls. Scoring was conducted with the H-score method, calculated by: $\Sigma(u \times \alpha)$, where u was the staining intensity (0-3+), and $\alpha$ was the percentage (0-100) of tumor cells stained with each intensity (ref).

Statistics

Event-time distributions were estimated using Kaplan-Meier analysis. Association of genotype with time to event outcome (PFS & OS) was evaluated using Cox's proportional hazards method. A significance level=0.017 corresponded to an overall type I error rate of 0.05 for each polymorphism, based on Bonferroni correction for multiple comparisons. Given a 1.7% false positive rate for each comparison, the probability that at least one false positive occurred among the 21 comparisons was about 0.3, assuming that all the comparisons were independent. Association of genotype with RR (defined as complete response/partial response vs. stable disease/progressive disease) and toxicity (grade 3/4 hypertension) was evaluated using Fisher's exact test with a significance level of p=0.05. Association of genotype with expression was studied using the Kruskal-wallis test. For RR and toxicity, given a 5% false positive rate for each comparison, the probability that at least one false positive occurred among the 7 comparisons was about 0.3, assuming that all the comparisons were independent. Associations of expression with time to event outcome (PFS & OS) and RR were evaluated using Cox's proportional hazards method and Wilcoxon rank-sum test, respectively. All p-values were two sided.

Relationship of Genotype with Efficacy

All candidate genotypes (Table 1) were compared with efficacy in both the control arm (paclitaxel alone) and the combination arm (paclitaxel and bevacizumab) as assessed in E2100. The efficacy parameters included PFS (primary endpoint of E2100), OS, and RR. The VEGF −2578 AA genotype and the VEGF −1154 AA genotypes predicted a favorable OS (Table 2) for patients in the combination arm.

TABLE 2

| | Relationship of VEGF genotype on overall survival (OS) | | | |
|---|---|---|---|---|
| SNP | Genotype comparison (median OS in months & frequency) | Hazard ratio | Confidence Interval | p-value |
| VEGF −2578 | CA (24.4; 42.6%) vs. AA (37.0; 20.8%) | 1.78 | (98.3% = 0.96, 3.32) | 0.026 |
| | CC (22.2; 37.6%) vs. AA (37.0; 21%) | 1.70 | (98.3% = 0.91, 3.17) | 0.043 |
| | CC (22.2; 37.6%) vs. CA (24.4; 42.6%) | 0.99 | (98.3% = 0.62, 1.58) | 0.95 |
| | AA vs. CA + CC | 0.58 | (95% = 0.36, 0.93) | 0.023 |
| VEGF −1154 | GG (22.3; 56.9%) vs. GA (29.8; 38.8%) | 1.60 | (98.3% = 0.98, 2.60) | 0.022 |
| | GG (22.3; 56.95) vs. AA (46.5; 9.4%) | 2.69 | (98.3% = 1.10, 6.59) | 0.008 |
| | GA (29.8; 38.8%) vs. AA (46.5; 9.4%) | 1.68 | (98.3% = 0.66, 4.30) | 0.19 |
| | AA vs. GA vs. GG | 0.62 | (95% = 0.46, 0.83) | 0.001 |

These genotypes did not predict an improved OS for patients in the control arm and did not predict a superior PFS nor RR for either arm. Because of the significant improvement for those with the VEGF −2578 AA genotype, we analyzed AA compared with the CA and CC combined genotypes for OS and this comparison demonstrated a hazard ratio of 0.58 (95% C.I.: 0.36, 0.93; p=0.023) in favor of the AA genotype. The corresponding PFS comparison revealed a hazard ratio of 0.91 (95% C.I. 0.62, 1.35; p=0.65) in favor of the VEGF −2578 AA genotype. Because of an apparent gene-dose effect in the VEGF −1154 SNP, we evaluated for a gene-dose effect and this demonstrated a hazard ratio of 0.62 (95% C.I.: 0.46; 0.83; p=0.001) in favor of the VEGF −1154AA genotype. This same gene-dose analysis for PFS revealed a hazard ratio of 0.79 (95% C.I.: 0.62, 1.02; p=0.07) in favor of the VEGF −1154AA genotype (Table 3).

TABLE 3

Relationship of VEGF genotype on progression free survival (PFS)

| SNP | Genotype comparison (median PFS in months) | Hazard ratio | Confidence Interval | p-value |
| --- | --- | --- | --- | --- |
| VEGF −1154 | AA (14.1) vs. GA (13.5) vs. GG (10.7) | 0.79 | (95% = 0.62, 1.02) | 0.07 |

The median overall survival for the control arm was 25.2 months and 26.7 months for the combination arm. The overall survival for the VEGF −2578 AA and the VEGF −1154 AA genotypes in the combination arm were significantly longer at 37.0 months and 46.5 months, respectively.

We also combined all genotypes for VEGF −2578 and VEGF −1154 and evaluated for an association with overall survival. There were 9 possible combinations of which four groups had 3 or fewer cases and therefore were excluded from the analysis. The remaining 5 groups were analyzed in relationship to survival (Table 4). When comparing the VEGF −2578/−1154 AA/AA genotype to all the others there was a statistically significant improvement in overall survival (p=0.041).

TABLE 4

Comparison of combined VEGF genotypes with overall survival

| VEGF genotypes −2578/−1154 | Median overall survival in months | % of cases | Comparison with other genotypes combined |
| --- | --- | --- | --- |
| AA/AA | 49.7 | 7.6 | P = 0.041 |
| AA/GA | 30.2 | 11.4 | p = 0.44 |
| CA/GA | 27.1 | 20.9 | p = 0.40 |
| CA/GG | 22.5 | 21.5 | p = 0.038 |
| CC/GG | 21.7 | 32.9 | p = 0.30 |
| Others | — | 5.7 | |

Relationship of Genotype with Toxicity (Grade 3/4 Hypertension)

All candidate genotypes (Table 1) were compared with the most common, significant toxicity, grade 3/4 hypertension (by Common Toxicity Criteria). Over 15% of all patients receiving bevacizumab in the parent trial experienced grade 3/4 hypertension. We observed that specific alleles at both VEGF −1498C/T and −634G/C were associated with grade 3/4 hypertension in the experimental arm. The VEGF −634 CC and VEGF −1498 TT genotypes strongly correlated with less grade 3/4 hypertension (8% and 0%, respectively) when compared to the alternate genotypes (Table 5). There was numerically less hypertension in the VEGF −2578 CC genotype (12%) when compared to the CA (21%) and AA (22%) genotypes but this did not reach statistical significance (p=0.32). When comparing the VEGF −2578 CC vs. the combined alternate genotypes (CA/AA) there was a trend for association (p=0.16). In similar fashion, the VEGF −1154 GG genotype had less hypertension (14%) compared with the combined alternate genotypes of GA (22%) and GG (27%) but this did not reach statistical significance (p=0.15).

TABLE 5

Relationship of VEGF genotype with grade 3/4 hypertension

| Single Nucleotide Polymorphism | % grade 3/4 hypertension & (absolute number/percentage) by genotype | p-value |
| --- | --- | --- |
| VEGF −634 | CC = 0% (n = 27; 15.3%) vs. GC = 22% (n = 82; 46.3%) vs. GG = 19% (n = 68; 38.4%) | 0.013 |
| | CC vs. GC + GG | 0.005 |
| VEGF −1498 | TT = 8% (n = 60; 33.9%) vs. CT = 22% (n = 82; 46.3%) vs. CC = 23% (n = 35; 19.8%) | 0.056 |
| | TT vs. CC + CT | 0.022 |

Relationship of Genotype with Expression (IHC)

All candidate genotypes (Table 1) were compared with primary tumor expression (assessed by IHC) for both VEGF and VEGFR-2. The degree of VEGF expression was evaluated by VEGF_inv score which ranged from 0 to 100 (based on the percentage of invasive cells with cytoplasmic VEGF staining). The degree of VEGFR-2 expression was evaluated by an H-score which could range from 0 (no detected expression) to 300 (100% of the cells had maximum 3+ expression). The genotypes were compared to VEGF expression for the entire cohort and there were no statistically significant associations determined. For the VEGF −2578 genotype there was a trend for an association between genotype and VEGF inv_score. The mean score for the AA genotype was lower (AA=48 (standard deviation=40)) when compared to the alternate genotypes (CA=54 (standard deviation=37) and CC=61 (standard deviation=37)) but this did not reach statistical significance (p=0.08). The VEGF −1154 AA genotype also had a lower mean expression (AA=42 (standard deviation=40)) than the alternate genotypes (GA=53 (standard deviation=38) and GG=58 (standard deviation=37)) but this also did not reach statistical significance (p=0.13). No genotypes correlated with the expression of VEGFR-2.

Relationship of VEGF and VEGFR-2 Expression with Clinical Outcome

Primary tumor expression (assessed by IHC) was compared with outcome in E2100 (RR, PFS and OS). There was no statistically significant association between either VEGF or VEGFR-2 expression with outcome. This was true when evaluating the control arm, the combination arm, or the entire cohort.

What is claimed is:

1. A method of treating a human patient suffering from breast cancer, the method comprising:
    (a) obtaining a sample containing nucleic acid isolated from the patient;
    (b) performing a genotyping assay on the sample and detecting the AA genotype at VEGF (−1154G/A) in said patient;

(c) identifying said patient having the AA genotype at VEGF (−1154G/A) as having an increased likelihood of benefiting from treatment with bevacizumab; and
(d) administering bevacizumab to the patient.

2. The method of claim 1, further comprising administering an anti-neoplastic composition.

3. The method of claim 1, wherein said breast cancer is metastatic breast cancer.

* * * * *